US008419727B2

(12) United States Patent
Koss et al.

(10) Patent No.: US 8,419,727 B2
(45) Date of Patent: Apr. 16, 2013

(54) IMPEDANCE MEDIATED POWER DELIVERY FOR ELECTROSURGERY

(75) Inventors: Tim Koss, Discovery Bay, CA (US); Miriam H. Taimisto, San Jose, CA (US); Roseanne Varner, Las Vegas, NV (US)

(73) Assignee: Aesculap AG, Tuttlingen (DE)

( * ) Notice: Subject to any disclaimer, the term of this patent is extended or adjusted under 35 U.S.C. 154(b) by 455 days.

(21) Appl. No.: 12/748,229

(22) Filed: Mar. 26, 2010

(65) Prior Publication Data
US 2011/0238062 A1 Sep. 29, 2011

(51) Int. Cl.
*A61B 18/14* (2006.01)

(52) U.S. Cl.
USPC .................................. 606/34; 606/41; 606/51

(58) Field of Classification Search .............. 606/32–35, 606/41, 48–50
See application file for complete search history.

(56) References Cited

U.S. PATENT DOCUMENTS

| | | |
|---|---|---|
| 3,356,408 A | 12/1967 | Stutz |
| 3,527,224 A | 9/1970 | Rabinowitz |
| 3,709,215 A | 1/1973 | Richmond |
| 3,742,955 A | 7/1973 | Battista et al. |
| 3,845,771 A | 11/1974 | Vise |
| 3,920,021 A | 11/1975 | Hiltebrandt |
| 3,970,088 A | 7/1976 | Morrison |
| 4,018,230 A | 4/1977 | Ochiai et al. |
| 4,041,952 A | 8/1977 | Morrison, Jr. et al. |
| 4,072,153 A | 2/1978 | Swartz |
| 4,094,320 A | 6/1978 | Newton et al. |
| 4,231,372 A | 11/1980 | Newton |
| 4,492,231 A | 1/1985 | Auth |
| 4,532,924 A | 8/1985 | Auth et al. |
| 4,590,934 A | 5/1986 | Malis et al. |
| 4,671,274 A | 6/1987 | Sorochenko |
| 4,972,846 A | 11/1990 | Owens et al. |
| 4,976,717 A | 12/1990 | Boyle |

(Continued)

FOREIGN PATENT DOCUMENTS

| | | |
|---|---|---|
| CA | 2061215 A1 | 8/1992 |
| EP | 0440385 A2 | 8/1991 |

(Continued)

OTHER PUBLICATIONS

Nezhat et al.; U.S. Appl. No. 08/948,282 entitled "Method and systems for organ resection," filed Oct. 9, 1997.

(Continued)

*Primary Examiner* — Michael Peffley
(74) *Attorney, Agent, or Firm* — RatnerPrestia

(57) ABSTRACT

An adaptive algorithm monitors the rate of tissue impedance change during an electrosurgical procedure. Impedance levels are examined to determine an impedance ramp and/or slope rate, which indicates the rate at which a target tissue is undergoing a phase or state change. The level of electrosurgical energy applied to the target tissue is adjusted in real time. Energy is applied to the target tissue at levels that allow tissue phase or state change to occur in an optimum fashion. Undesired results such as thermal damage and defective sealing are mitigated. Another embodiment determines impedance achieved within a specific interval and adjusts the electrosurgical energy applied to the tissue after a threshold impedance has been maintained or exceeded for a predetermined interval. A further aspect of the invention provides mitigation during processing for partial tissue coverage of device electrodes or thin tissue.

12 Claims, 8 Drawing Sheets

U.S. PATENT DOCUMENTS

| | | |
|---|---|---|
| 4,979,948 A | 12/1990 | Geddes et al. |
| 4,998,527 A | 3/1991 | Meyer |
| 5,037,379 A | 8/1991 | Clayman et al. |
| 5,041,101 A | 8/1991 | Seder et al. |
| 5,059,782 A | 10/1991 | Fukuyama |
| 5,078,736 A | 1/1992 | Behl |
| 5,108,408 A | 4/1992 | Lally |
| 5,133,713 A | 7/1992 | Huang et al. |
| 5,151,102 A | 9/1992 | Kamiyama et al. |
| 5,156,613 A | 10/1992 | Sawyer |
| 5,178,618 A | 1/1993 | Kandarpa |
| 5,190,541 A | 3/1993 | Abele et al. |
| 5,207,691 A | 5/1993 | Nardella |
| 5,217,030 A | 6/1993 | Yoon |
| 5,234,425 A | 8/1993 | Fogarty et al. |
| 5,250,074 A | 10/1993 | Wilk et al. |
| 5,267,998 A | 12/1993 | Hagen |
| 5,269,780 A | 12/1993 | Roos |
| 5,269,782 A | 12/1993 | Sutter |
| 5,273,524 A | 12/1993 | Fox et al. |
| 5,277,201 A | 1/1994 | Stern |
| 5,281,216 A | 1/1994 | Klicek |
| 5,282,799 A | 2/1994 | Rydell |
| 5,290,287 A | 3/1994 | Boebel et al. |
| 5,295,990 A | 3/1994 | Levin |
| 5,300,068 A | 4/1994 | Rosar et al. |
| 5,300,087 A | 4/1994 | Knoepfler |
| 5,312,023 A | 5/1994 | Green et al. |
| 5,324,289 A | 6/1994 | Eggers |
| 5,330,471 A | 7/1994 | Eggers |
| 5,330,502 A | 7/1994 | Hassler et al. |
| 5,336,229 A | 8/1994 | Noda |
| 5,336,237 A | 8/1994 | Chin et al. |
| 5,341,807 A | 8/1994 | Nardella |
| 5,342,381 A | 8/1994 | Tidemand |
| 5,352,223 A | 10/1994 | McBrayer et al. |
| 5,352,235 A | 10/1994 | Koros et al. |
| 5,354,336 A | 10/1994 | Kelman et al. |
| 5,356,408 A | 10/1994 | Rydell |
| 5,374,277 A | 12/1994 | Hassler |
| 5,377,415 A | 1/1995 | Gibson |
| 5,391,166 A | 2/1995 | Eggers |
| 5,395,369 A | 3/1995 | McBrayer et al. |
| 5,396,900 A | 3/1995 | Slater et al. |
| 5,397,320 A | 3/1995 | Essig et al. |
| 5,403,312 A | 4/1995 | Yates et al. |
| 5,417,687 A | 5/1995 | Nardella et al. |
| 5,423,814 A | 6/1995 | Zhu et al. |
| 5,431,676 A | 7/1995 | Dubrul et al. |
| 5,438,302 A | 8/1995 | Goble |
| 5,443,463 A | 8/1995 | Stern et al. |
| 5,443,470 A | 8/1995 | Stern et al. |
| 5,445,638 A | 8/1995 | Rydell et al. |
| 5,447,513 A | 9/1995 | Davison et al. |
| 5,449,355 A | 9/1995 | Rhum et al. |
| 5,456,684 A | 10/1995 | Schmidt et al. |
| 5,458,598 A | 10/1995 | Feinberg et al. |
| 5,462,546 A | 10/1995 | Rydell |
| 5,472,442 A | 12/1995 | Klicek |
| 5,480,399 A | 1/1996 | Hebborn |
| 5,482,054 A | 1/1996 | Slater et al. |
| 5,484,435 A | 1/1996 | Fleenor et al. |
| 5,484,436 A | 1/1996 | Eggers et al. |
| 5,496,312 A | 3/1996 | Klicek |
| 5,496,317 A | 3/1996 | Goble et al. |
| 5,514,134 A | 5/1996 | Rydell et al. |
| 5,520,698 A | 5/1996 | Koh |
| 5,531,744 A | 7/1996 | Nardella et al. |
| 5,540,684 A | 7/1996 | Hassler, Jr. |
| 5,540,685 A | 7/1996 | Parins et al. |
| 5,542,945 A | 8/1996 | Fritzsch |
| 5,549,637 A | 8/1996 | Crainich |
| 5,556,397 A | 9/1996 | Long et al. |
| 5,558,100 A | 9/1996 | Cox |
| 5,558,671 A | 9/1996 | Yates |
| 5,562,700 A | 10/1996 | Huitema et al. |
| 5,562,701 A | 10/1996 | Huitema et al. |
| 5,562,702 A | 10/1996 | Huitema et al. |
| 5,562,720 A | 10/1996 | Stern et al. |
| 5,569,243 A | 10/1996 | Kortenbach et al. |
| 5,571,100 A | 11/1996 | Goble et al. |
| 5,573,535 A | 11/1996 | Viklund |
| 5,578,052 A | 11/1996 | Koros et al. |
| 5,599,350 A | 2/1997 | Schulze et al. |
| 5,601,224 A | 2/1997 | Bishop et al. |
| 5,603,700 A | 2/1997 | Daneshvar |
| 5,603,711 A | 2/1997 | Parins et al. |
| 5,611,803 A | 3/1997 | Heaven et al. |
| 5,624,452 A | 4/1997 | Yates |
| 5,637,110 A | 6/1997 | Pennybacker et al. |
| 5,637,111 A | 6/1997 | Sutcu et al. |
| 5,653,692 A | 8/1997 | Masterson et al. |
| 5,658,281 A | 8/1997 | Heard |
| 5,662,662 A | 9/1997 | Bishop et al. |
| 5,662,676 A | 9/1997 | Koninckx |
| 5,665,085 A | 9/1997 | Nardella |
| 5,665,100 A | 9/1997 | Yoon |
| 5,667,526 A | 9/1997 | Levin |
| 5,669,907 A | 9/1997 | Platt, Jr. et al. |
| 5,673,840 A | 10/1997 | Schulze et al. |
| 5,673,841 A | 10/1997 | Schulze et al. |
| 5,674,184 A | 10/1997 | Hassler, Jr. |
| 5,674,220 A | 10/1997 | Fox et al. |
| 5,675,184 A | 10/1997 | Matsubayashi et al. |
| 5,680,982 A | 10/1997 | Schulze et al. |
| 5,681,282 A | 10/1997 | Eggers et al. |
| 5,683,385 A | 11/1997 | Kortenbach et al. |
| 5,683,388 A | 11/1997 | Slater |
| 5,688,270 A | 11/1997 | Yates et al. |
| 5,693,051 A | 12/1997 | Schulze et al. |
| 5,697,949 A | 12/1997 | Giurtino et al. |
| 5,700,261 A | 12/1997 | Brinkerhoff |
| 5,702,390 A | 12/1997 | Austin et al. |
| 5,704,534 A | 1/1998 | Huitema et al. |
| 5,707,369 A | 1/1998 | Vaitekunas et al. |
| 5,709,680 A | 1/1998 | Yates et al. |
| 5,713,896 A | 2/1998 | Nardella |
| 5,715,832 A | 2/1998 | Koblish et al. |
| 5,718,703 A | 2/1998 | Chin |
| 5,720,719 A | 2/1998 | Edwards et al. |
| 5,728,143 A | 3/1998 | Gough et al. |
| 5,733,283 A | 3/1998 | Malis et al. |
| 5,735,289 A | 4/1998 | Pfeffer et al. |
| 5,735,848 A | 4/1998 | Yates et al. |
| 5,735,849 A | 4/1998 | Baden et al. |
| 5,741,285 A | 4/1998 | McBrayer et al. |
| 5,746,750 A | 5/1998 | Prestel et al. |
| 5,749,895 A | 5/1998 | Sawyer et al. |
| 5,755,717 A | 5/1998 | Yates et al. |
| 5,776,130 A | 7/1998 | Buysse et al. |
| 5,788,662 A | 8/1998 | Antanavich et al. |
| 5,797,941 A | 8/1998 | Schulze et al. |
| 5,810,811 A | 9/1998 | Yates et al. |
| 5,817,091 A | 10/1998 | Nardella et al. |
| 5,817,092 A | 10/1998 | Behl |
| 5,823,066 A | 10/1998 | Huitema et al. |
| 5,827,271 A * | 10/1998 | Buysse et al. .................. 606/40 |
| 5,833,689 A | 11/1998 | Long |
| 5,836,990 A | 11/1998 | Li |
| 5,840,077 A | 11/1998 | Rowden et al. |
| 5,855,576 A | 1/1999 | LeVeen et al. |
| 5,860,975 A | 1/1999 | Goble et al. |
| 5,891,142 A | 4/1999 | Eggers et al. |
| 5,893,835 A | 4/1999 | Witt et al. |
| 5,893,874 A | 4/1999 | Bourque et al. |
| 5,931,835 A | 8/1999 | Mackey |
| 5,931,836 A | 8/1999 | Hatta et al. |
| 5,954,720 A | 9/1999 | Wilson et al. |
| 5,976,128 A | 11/1999 | Schilling et al. |
| 5,979,453 A | 11/1999 | Savage et al. |
| 6,003,517 A | 12/1999 | Sheffield et al. |
| 6,004,319 A | 12/1999 | Goble et al. |
| 6,030,384 A | 2/2000 | Nezhat |
| 6,050,993 A | 4/2000 | Tu et al. |
| 6,050,995 A | 4/2000 | Durgin |
| 6,056,744 A | 5/2000 | Edwards |
| 6,059,766 A | 5/2000 | Greff |

| Patent No. | Date | Inventor |
|---|---|---|
| 6,059,782 A | 5/2000 | Novak et al. |
| 6,066,139 A | 5/2000 | Ryan et al. |
| 6,068,626 A | 5/2000 | Harrington et al. |
| 6,071,281 A | 6/2000 | Burnside et al. |
| 6,074,386 A | 6/2000 | Goble et al. |
| 6,080,149 A * | 6/2000 | Huang et al. .............. 606/32 |
| 6,086,586 A | 7/2000 | Hooven |
| 6,090,106 A | 7/2000 | Goble et al. |
| 6,093,186 A | 7/2000 | Goble |
| 6,096,037 A | 8/2000 | Mulier et al. |
| 6,099,550 A | 8/2000 | Yoon |
| 6,123,701 A | 9/2000 | Nezhat |
| H1904 H | 10/2000 | Yates et al. |
| 6,142,992 A | 11/2000 | Cheng et al. |
| 6,152,920 A | 11/2000 | Thompson et al. |
| 6,152,932 A | 11/2000 | Ternstrom |
| 6,162,220 A | 12/2000 | Nezhat |
| 6,174,309 B1 | 1/2001 | Wrublewski et al. |
| 6,179,832 B1 | 1/2001 | Jones et al. |
| 6,203,541 B1 | 3/2001 | Keppel |
| 6,203,542 B1 | 3/2001 | Ellsberry et al. |
| 6,206,877 B1 | 3/2001 | Kese et al. |
| 6,210,406 B1 | 4/2001 | Webster |
| 6,212,426 B1 | 4/2001 | Swanson |
| 6,217,894 B1 | 4/2001 | Sawhney et al. |
| 6,228,084 B1 | 5/2001 | Kirwan, Jr. |
| 6,234,178 B1 | 5/2001 | Goble et al. |
| 6,241,139 B1 | 6/2001 | Milliman et al. |
| 6,245,069 B1 | 6/2001 | Gminder |
| 6,254,601 B1 | 7/2001 | Burbank et al. |
| 6,258,085 B1 | 7/2001 | Eggleston |
| 6,277,114 B1 | 8/2001 | Bullivant et al. |
| 6,283,963 B1 | 9/2001 | Regula |
| 6,287,304 B1 | 9/2001 | Eggers et al. |
| 6,290,715 B1 | 9/2001 | Sharkey et al. |
| 6,293,942 B1 | 9/2001 | Goble et al. |
| 6,293,946 B1 | 9/2001 | Thorne |
| 6,296,636 B1 | 10/2001 | Cheng et al. |
| 6,312,430 B1 | 11/2001 | Wilson et al. |
| 6,322,494 B1 | 11/2001 | Bullivant et al. |
| 6,327,505 B1 | 12/2001 | Medhkour et al. |
| 6,334,861 B1 | 1/2002 | Chandler et al. |
| 6,350,274 B1 | 2/2002 | Li |
| 6,361,559 B1 | 3/2002 | Houser et al. |
| 6,364,879 B1 | 4/2002 | Chen et al. |
| 6,371,956 B1 | 4/2002 | Wilson et al. |
| 6,391,024 B1 | 5/2002 | Sun et al. |
| 6,391,029 B1 | 5/2002 | Hooven et al. |
| 6,398,779 B1 | 6/2002 | Buysse et al. |
| 6,398,781 B1 | 6/2002 | Goble et al. |
| 6,409,722 B1 * | 6/2002 | Hoey et al. .............. 606/34 |
| H2037 H | 7/2002 | Yates et al. |
| 6,416,509 B1 | 7/2002 | Goble et al. |
| 6,428,550 B1 | 8/2002 | Vargas et al. |
| 6,436,096 B1 | 8/2002 | Hareyama |
| 6,464,702 B2 | 10/2002 | Schulze et al. |
| 6,485,486 B1 | 11/2002 | Trembly et al. |
| 6,485,489 B2 | 11/2002 | Teirstein et al. |
| 6,491,690 B1 | 12/2002 | Goble et al. |
| 6,494,881 B1 | 12/2002 | Bales et al. |
| 6,500,176 B1 | 12/2002 | Truckai et al. |
| 6,514,252 B2 | 2/2003 | Nezhat et al. |
| 6,517,530 B1 | 2/2003 | Kleven |
| 6,520,185 B1 | 2/2003 | Bommannan et al. |
| 6,533,784 B2 | 3/2003 | Truckai et al. |
| 6,546,933 B1 | 4/2003 | Yoon |
| 6,554,829 B2 | 4/2003 | Schulze et al. |
| 6,564,806 B1 | 5/2003 | Fogarty et al. |
| 6,565,560 B1 | 5/2003 | Goble et al. |
| 6,565,561 B1 | 5/2003 | Goble et al. |
| 6,584,360 B2 | 6/2003 | Francischelli et al. |
| 6,610,074 B2 | 8/2003 | Santilli |
| 6,616,654 B2 | 9/2003 | Mollenauer |
| 6,616,659 B1 | 9/2003 | de la Torre et al. |
| 6,619,529 B2 | 9/2003 | Green et al. |
| 6,623,482 B2 | 9/2003 | Pendekanti et al. |
| 6,626,901 B1 | 9/2003 | Treat et al. |
| 6,645,198 B1 | 11/2003 | Bommannan et al. |
| 6,645,201 B1 | 11/2003 | Utley et al. |
| 6,648,839 B2 | 11/2003 | Manna et al. |
| 6,652,518 B2 | 11/2003 | Wellman et al. |
| 6,656,177 B2 | 12/2003 | Truckai et al. |
| 6,666,859 B1 | 12/2003 | Fleenor et al. |
| 6,673,085 B1 | 1/2004 | Berg |
| 6,676,660 B2 | 1/2004 | Wampler et al. |
| 6,682,526 B1 | 1/2004 | Jones et al. |
| 6,682,527 B2 | 1/2004 | Strul |
| 6,695,840 B2 | 2/2004 | Schulze |
| 6,699,245 B2 | 3/2004 | Dinger et al. |
| 6,719,754 B2 | 4/2004 | Underwood et al. |
| 6,722,371 B1 | 4/2004 | Fogarty et al. |
| 6,736,814 B2 | 5/2004 | Manna et al. |
| 6,743,229 B2 | 6/2004 | Buysse et al. |
| 6,746,488 B1 | 6/2004 | Bales |
| 6,752,154 B2 | 6/2004 | Fogarty et al. |
| 6,752,803 B2 | 6/2004 | Goldman et al. |
| 6,770,070 B1 | 8/2004 | Balbierz |
| 6,770,072 B1 | 8/2004 | Truckai et al. |
| 6,808,525 B2 | 10/2004 | Latterell et al. |
| 6,817,974 B2 | 11/2004 | Cooper et al. |
| 6,821,273 B2 | 11/2004 | Mollenauer |
| 6,837,888 B2 | 1/2005 | Ciarrocca et al. |
| 6,840,938 B1 | 1/2005 | Morley et al. |
| 6,843,789 B2 | 1/2005 | Goble |
| 6,852,108 B2 | 2/2005 | Barry et al. |
| 6,889,089 B2 | 5/2005 | Behl et al. |
| 6,893,435 B2 | 5/2005 | Goble |
| 6,896,672 B1 | 5/2005 | Eggers et al. |
| 6,896,673 B2 | 5/2005 | Hooven |
| 6,905,506 B2 | 6/2005 | Burbank et al. |
| 6,913,579 B2 | 7/2005 | Truckai et al. |
| 6,918,907 B2 | 7/2005 | Kelly et al. |
| 6,918,909 B2 | 7/2005 | Ohyama et al. |
| 6,923,803 B2 | 8/2005 | Goble |
| 6,926,712 B2 | 8/2005 | Phan |
| 6,929,642 B2 | 8/2005 | Xiao et al. |
| 6,936,048 B2 | 8/2005 | Hurst |
| 6,939,346 B2 | 9/2005 | Kannenberg et al. |
| 6,953,461 B2 | 10/2005 | McClurken et al. |
| 6,981,628 B2 | 1/2006 | Wales |
| 7,033,356 B2 | 4/2006 | Latterell et al. |
| 7,063,699 B2 | 6/2006 | Hess et al. |
| 7,090,637 B2 | 8/2006 | Danitz et al. |
| 7,090,673 B2 | 8/2006 | Dycus et al. |
| 7,090,685 B2 | 8/2006 | Kortenbach et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,118,587 B2 | 10/2006 | Dycus et al. |
| 7,125,409 B2 | 10/2006 | Truckai et al. |
| 7,137,980 B2 | 11/2006 | Buysse et al. |
| 7,159,750 B2 | 1/2007 | Racenet et al. |
| 7,166,102 B2 | 1/2007 | Fleenor et al. |
| 7,169,146 B2 | 1/2007 | Truckai et al. |
| 7,179,254 B2 | 2/2007 | Pendekanti et al. |
| 7,195,627 B2 | 3/2007 | Amoah et al. |
| 7,220,260 B2 | 5/2007 | Fleming et al. |
| 7,238,195 B2 | 7/2007 | Viola |
| 7,250,048 B2 | 7/2007 | Francischelli et al. |
| 7,267,677 B2 | 9/2007 | Johnson et al. |
| 7,270,664 B2 | 9/2007 | Johnson et al. |
| 7,276,068 B2 | 10/2007 | Johnson et al. |
| 7,278,991 B2 | 10/2007 | Morris et al. |
| 7,291,143 B2 | 11/2007 | Swanson |
| 7,364,577 B2 | 4/2008 | Wham et al. |
| 7,367,972 B2 | 5/2008 | Francischelli et al. |
| 7,410,483 B2 | 8/2008 | Danitz et al. |
| 7,494,039 B2 | 2/2009 | Racenet et al. |
| 7,506,790 B2 | 3/2009 | Shelton, IV et al. |
| 7,540,872 B2 | 6/2009 | Schechter et al. |
| 7,549,564 B2 | 6/2009 | Boudreaux |
| 7,624,902 B2 | 12/2009 | Marczyk et al. |
| 7,641,651 B2 | 1/2010 | Nezhat et al. |
| 7,703,653 B2 | 4/2010 | Shah et al. |
| 7,722,601 B2 * | 5/2010 | Wham et al. .............. 606/34 |
| 7,794,461 B2 | 9/2010 | Eder et al. |
| 7,803,156 B2 | 9/2010 | Eder et al. |

| | | |
|---|---|---|
| 7,862,565 B2 | 1/2011 | Eder et al. |
| 2001/0029367 A1 | 10/2001 | Fleenor et al. |
| 2002/0062123 A1 | 5/2002 | McClurken et al. |
| 2002/0062136 A1 | 5/2002 | Hillstead et al. |
| 2002/0107514 A1 | 8/2002 | Hooven |
| 2002/0124853 A1 | 9/2002 | Burbank et al. |
| 2002/0128643 A1 | 9/2002 | Simpson et al. |
| 2002/0151882 A1 | 10/2002 | Marko et al. |
| 2002/0177848 A1 | 11/2002 | Truckai et al. |
| 2002/0183738 A1 | 12/2002 | Chee et al. |
| 2003/0078577 A1 | 4/2003 | Truckai et al. |
| 2003/0144652 A1 | 7/2003 | Baker et al. |
| 2003/0144653 A1 | 7/2003 | Francischelli et al. |
| 2003/0158547 A1 | 8/2003 | Phan |
| 2003/0171745 A1 | 9/2003 | Francischelli et al. |
| 2003/0216726 A1 | 11/2003 | Eggers et al. |
| 2003/0229344 A1 | 12/2003 | Dycus et al. |
| 2003/0236549 A1 | 12/2003 | Bonadio et al. |
| 2004/0006339 A1 | 1/2004 | Underwood et al. |
| 2004/0010245 A1 | 1/2004 | Cerier et al. |
| 2004/0068274 A1 | 4/2004 | Hooven |
| 2004/0097919 A1 | 5/2004 | Wellman et al. |
| 2004/0122423 A1 | 6/2004 | Dycus et al. |
| 2004/0143263 A1 | 7/2004 | Schechter et al. |
| 2004/0199226 A1 | 10/2004 | Shadduck |
| 2004/0236320 A1 | 11/2004 | Protsenko et al. |
| 2005/0010212 A1 | 1/2005 | McClurken et al. |
| 2005/0015085 A1 | 1/2005 | McClurken et al. |
| 2005/0021026 A1 | 1/2005 | Baily |
| 2005/0021027 A1 | 1/2005 | Shields et al. |
| 2005/0033276 A1 | 2/2005 | Adachi |
| 2005/0033277 A1 | 2/2005 | Clague et al. |
| 2005/0033278 A1 | 2/2005 | McClurken et al. |
| 2005/0070895 A1 | 3/2005 | Ryan et al. |
| 2005/0070978 A1 | 3/2005 | Bek et al. |
| 2005/0090819 A1 | 4/2005 | Goble |
| 2005/0096645 A1 | 5/2005 | Wellman et al. |
| 2005/0096694 A1 | 5/2005 | Lee |
| 2005/0107781 A1 | 5/2005 | Ostrovsky et al. |
| 2005/0107784 A1 | 5/2005 | Moses et al. |
| 2005/0113817 A1 | 5/2005 | Isaacson et al. |
| 2005/0113820 A1 | 5/2005 | Goble et al. |
| 2005/0119654 A1 | 6/2005 | Swanson et al. |
| 2005/0131390 A1 | 6/2005 | Heinrich et al. |
| 2005/0149073 A1 | 7/2005 | Arani et al. |
| 2005/0171533 A1 | 8/2005 | Latterell et al. |
| 2005/0187561 A1 | 8/2005 | Lee-Sepsick et al. |
| 2005/0192633 A1 | 9/2005 | Montpetit |
| 2005/0196421 A1 | 9/2005 | Hunter et al. |
| 2005/0203500 A1 | 9/2005 | Saadat et al. |
| 2005/0203504 A1 | 9/2005 | Wham et al. |
| 2005/0209664 A1 | 9/2005 | Hunter et al. |
| 2005/0226682 A1 | 10/2005 | Chersky et al. |
| 2005/0256522 A1 | 11/2005 | Francischelli et al. |
| 2005/0256524 A1 | 11/2005 | Long et al. |
| 2005/0261676 A1 | 11/2005 | Hall et al. |
| 2006/0025765 A1 | 2/2006 | Landman et al. |
| 2006/0025812 A1 | 2/2006 | Shelton, IV |
| 2006/0041254 A1 | 2/2006 | Francischelli et al. |
| 2006/0052778 A1 | 3/2006 | Chapman et al. |
| 2006/0052779 A1 | 3/2006 | Hammill |
| 2006/0064084 A1 | 3/2006 | Haemmerich et al. |
| 2006/0079872 A1 | 4/2006 | Eggleston |
| 2006/0167451 A1 | 7/2006 | Cropper |
| 2006/0190029 A1 | 8/2006 | Wales |
| 2006/0199999 A1 | 9/2006 | Ikeda et al. |
| 2006/0217709 A1 | 9/2006 | Couture et al. |
| 2006/0226196 A1 | 10/2006 | Hueil et al. |
| 2006/0229665 A1 | 10/2006 | Wales et al. |
| 2006/0253117 A1 | 11/2006 | Hovda et al. |
| 2006/0258954 A1 | 11/2006 | Timberlake et al. |
| 2006/0259034 A1 | 11/2006 | Eder et al. |
| 2006/0259035 A1 | 11/2006 | Nezhat et al. |
| 2006/0271037 A1 | 11/2006 | Maroney et al. |
| 2006/0271042 A1 | 11/2006 | Latterell et al. |
| 2006/0287674 A1 | 12/2006 | Ginn et al. |
| 2006/0289602 A1 | 12/2006 | Wales et al. |
| 2006/0293655 A1 | 12/2006 | Sartor |
| 2007/0005061 A1 | 1/2007 | Eder et al. |
| 2007/0062017 A1 | 3/2007 | Dycus et al. |
| 2007/0073340 A1 | 3/2007 | Shelton, IV et al. |
| 2007/0128174 A1 | 6/2007 | Kleinsek et al. |
| 2007/0129726 A1 | 6/2007 | Eder et al. |
| 2007/0173804 A1 | 7/2007 | Wham et al. |
| 2007/0173805 A1* | 7/2007 | Weinberg et al. ............... 606/34 |
| 2007/0173811 A1 | 7/2007 | Couture et al. |
| 2007/0179497 A1 | 8/2007 | Eggers et al. |
| 2007/0185482 A1 | 8/2007 | Eder et al. |
| 2007/0208333 A1* | 9/2007 | Uchida et al. ................... 606/34 |
| 2007/0244538 A1 | 10/2007 | Eder et al. |
| 2007/0250113 A1 | 10/2007 | Hegeman et al. |
| 2007/0265613 A1 | 11/2007 | Edelstein et al. |
| 2007/0282318 A1 | 12/2007 | Spooner et al. |
| 2007/0282320 A1 | 12/2007 | Buysse et al. |
| 2008/0172052 A1 | 7/2008 | Eder et al. |
| 2008/0188844 A1 | 8/2008 | McGreevy et al. |
| 2008/0195093 A1 | 8/2008 | Couture et al. |
| 2008/0221565 A1 | 9/2008 | Eder et al. |
| 2008/0228179 A1 | 9/2008 | Eder et al. |
| 2008/0275446 A1 | 11/2008 | Messerly |
| 2008/0308607 A1 | 12/2008 | Timm et al. |
| 2009/0138006 A1 | 5/2009 | Bales et al. |
| 2009/0157071 A1 | 6/2009 | Wham et al. |
| 2009/0157072 A1 | 6/2009 | Wham et al. |
| 2009/0157075 A1 | 6/2009 | Wham et al. |
| 2009/0182323 A1 | 7/2009 | Eder et al. |
| 2009/0198272 A1 | 8/2009 | Kerver et al. |
| 2009/0209953 A1 | 8/2009 | Schoenman |
| 2009/0240245 A1 | 9/2009 | Deville et al. |
| 2009/0299367 A1 | 12/2009 | Ginnebaugh et al. |
| 2010/0042093 A9 | 2/2010 | Wham et al. |
| 2010/0076427 A1 | 3/2010 | Heard |
| 2010/0094282 A1 | 4/2010 | Kabaya et al. |
| 2010/0280508 A1 | 11/2010 | Eder |
| 2010/0298823 A1 | 11/2010 | Cao et al. |
| 2011/0202058 A1 | 8/2011 | Eder et al. |

FOREIGN PATENT DOCUMENTS

| | | |
|---|---|---|
| EP | 0487269 A1 | 5/1992 |
| EP | 0502268 A1 | 9/1992 |
| EP | 0562195 A1 | 9/1993 |
| EP | 0658333 A1 | 6/1995 |
| EP | 0923907 A1 | 6/1999 |
| EP | 0833593 B1 | 2/2001 |
| EP | 0737446 B1 | 12/2002 |
| EP | 0717960 B1 | 2/2003 |
| EP | 0869742 B1 | 5/2003 |
| EP | 0873089 B1 | 10/2003 |
| EP | 0742696 B1 | 11/2003 |
| EP | 1041933 B1 | 3/2004 |
| EP | 1004277 B1 | 7/2004 |
| EP | 0959786 B1 | 9/2004 |
| EP | 0913126 B1 | 10/2004 |
| EP | 0956827 B1 | 10/2004 |
| EP | 1472984 A1 | 11/2004 |
| EP | 1621146 A2 | 2/2006 |
| EP | 1645237 A1 | 4/2006 |
| EP | 0875209 B1 | 5/2006 |
| EP | 1293170 B1 | 6/2006 |
| EP | 1293169 B1 | 7/2006 |
| EP | 1064886 B1 | 8/2006 |
| EP | 1767164 A1 | 3/2007 |
| EP | 1518498 B1 | 12/2007 |
| EP | 1862138 A1 | 12/2007 |
| EP | 1039862 B1 | 5/2008 |
| EP | 1532933 B1 | 5/2008 |
| EP | 1707143 B1 | 6/2008 |
| EP | 1518499 B1 | 8/2008 |
| EP | 1632192 B1 | 3/2009 |
| EP | 1486177 B1 | 8/2009 |
| EP | 1852081 B1 | 8/2009 |
| EP | 1747761 B1 | 10/2009 |
| EP | 2106764 A2 | 10/2009 |
| JP | 2003088534 | 3/2003 |
| JP | 2004049566 | 2/2004 |
| JP | 2005144193 | 6/2005 |
| WO | WO92/22257 A1 | 12/1992 |
| WO | WO93/08754 A1 | 5/1993 |

| | | |
|---|---|---|
| WO | WO94/00060 A1 | 1/1994 |
| WO | WO94/26179 A1 | 11/1994 |
| WO | WO95/02371 A2 | 1/1995 |
| WO | WO96/05776 A1 | 2/1996 |
| WO | WO96/16605 A1 | 6/1996 |
| WO | WO96/23449 A1 | 8/1996 |
| WO | WO97/24073 A1 | 7/1997 |
| WO | WO97/24074 A1 | 7/1997 |
| WO | WO98/12999 A2 | 4/1998 |
| WO | WO98/43548 A1 | 10/1998 |
| WO | WO98/53750 A1 | 12/1998 |
| WO | WO99/23933 A2 | 5/1999 |
| WO | WO99/52459 A1 | 10/1999 |
| WO | WO99/56646 A1 | 11/1999 |
| WO | WO00/13192 A1 | 3/2000 |
| WO | WO00/13193 A1 | 3/2000 |
| WO | WO01/12090 A1 | 2/2001 |
| WO | WO01/35846 A1 | 5/2001 |
| WO | WO01/54602 A2 | 8/2001 |
| WO | WO01/58372 A1 | 8/2001 |
| WO | WO01/58373 A1 | 8/2001 |
| WO | WO01/82812 A1 | 11/2001 |
| WO | WO02/24092 A1 | 3/2002 |
| WO | WO02/058542 A2 | 8/2002 |
| WO | WO02/067798 A1 | 9/2002 |
| WO | WO03/088806 A2 | 10/2003 |
| WO | WO03/103522 A1 | 12/2003 |
| WO | WO2004/032596 A2 | 4/2004 |
| WO | WO2004/032776 A1 | 4/2004 |
| WO | WO2004/073490 A2 | 9/2004 |
| WO | WO2004/098383 A2 | 11/2004 |
| WO | WO2005/009213 A2 | 2/2005 |
| WO | WO2005/034729 A2 | 4/2005 |
| WO | WO2005/079901 A1 | 9/2005 |
| WO | WO2005/115251 A1 | 12/2005 |
| WO | WO2006/060431 A1 | 6/2006 |
| WO | WO2007/002227 A2 | 1/2007 |
| WO | WO2007/082061 A2 | 7/2007 |
| WO | WO2008/094554 A2 | 8/2008 |
| WO | WO2008/124112 A1 | 10/2008 |

OTHER PUBLICATIONS

Eder, Joseph C.; U.S. Appl. No. 12/200,798 entitled "Assisted systems and methods for performing transvaginal hysterectomies," filed Aug. 28, 2008.
Koss et al.; U.S. Appl. No. 12/907,646 entitled "Impedance mediated control of power delivery for electrosurgery," filed Oct. 19, 2010.
Walberg, Erik; U.S. Appl. No. 13/021,633 entitled "Laparoscopic radiofrequency surgical device," filed Feb. 4, 2011.
(Arthrocare); Arthrocare receives clearance to market coblation-based devices for gynecology and laparoscopic surgery: clearance includes plasma forceps and 21 specific indications; Business Wire; p. 524; Oct. 25, 2001.
(Business Wire); Radiofrequency energy proven effective against leading cause of obstructive sleep apnea; Business Wire; p09140175; Sep. 14, 1998.
(Curon); Curon announces the publication of data supporting durability and effectiveness of STRETTA® system—positive one year follow-up data of U.S. clinical trial published in gastrointestinal endoscopy; PR Newswire; pNYTH10307022002; Feb. 7, 2002.
(Curon); Curon medical announces presentation of positive clinical study results of STRETTA® procedure for gastroesophageal reflux disease (GERD); PR Newswire; pNYW07920032002; Mar. 20, 2002.
(Enable); Enable medical introduces second generation bipolar scissors; Health Industry Today; pNA; Dec. 1998.
(Everest) Everest medical announces introduction of 3mm bipolar forceps; PR Newswire; p1002MNW021; Oct. 2, 1996.
(Everest) Everest medical discusses patent status: forecasts $1 million revenue first quarter: introduces next generation bipolar scissors; PR Newswire; pN/A; Mar. 31, 1994.
(Everest) Everest medical introduces new QUADRIPOLAR} cutting forceps at the global congress for gynecologic endoscopy meeting; PR Newswire; p. 8927; Nov. 8, 1999.
(Everest) Everest medical reports record first quarter results: introduces next generation bipolar scissors; PR Newswire; pN/A; Apr. 19, 1994.
(Everest) Quadripolar cutting forceps introduced by Everest Medical; Health Industry Today; vol. 63; No. 1; pNA; Jan. 2000.
(Novare); U.S. patent issued for Novare Surgical Systems Cygnet® surgical clamp: Novare signs multi-year supply agreement with Boston Scientific; PR Newswire; pNA; Sep. 2, 2003.
Aoki et al.; Thoracoscopic resection of the lung with the ultrasonic scalpel; Ann thorac Surg; vol. 67; No. 4; pp. 1181-1183; Apr. 1999.
Bergamaschi et al.; Laparoscopic intracorporeal bowel resection with ultrasound versus electrosurgical dissection; JSLS; vol. 5; No. 1; pp. 17-20; Jan.-Mar. 2001.
Eichfeld et al.; Evaluation of ultracision in lung metastatic surgery; Ann Thorac Surg; vol. 70; No. 4; pp. 1181-1184; Oct. 2000.
ERBE Elektromedizin GmbH; ERBE BiClamp Brochure; http://www.erbe-med.com/erbe/media/Marketingmaterialien/85100-139_ERBE_EN_BiClamp_D024676.pdf; downloaded Jan. 24, 2011; 6 pgs.
Gyrus ACMI (an Olympus Company); PKS Seal (product page); http://www.gyrusacmi.com/user/display.cfm?display=product&pid=9024; downloaded Jan. 24, 2011; 1 page.
GYRUS Medical; Cutting Forceps (Product Information); downloaded Oct. 5, 2005.
GYRUS Medical; LP Scissors (Product Information); downloaded Oct. 5, 2005.
GYRUS Medical; Lyons} Dissecting Forceps (Product Information); downloaded Oct. 5, 2005.
GYRUS Medical; Micro/Macro-Jaw Forceps (Product Information); downloaded Oct. 5, 2005.
GYRUS Medical; Seal} Open Forceps (Product Information); downloaded Oct. 5, 2005.
Hayashi et al.; Experimental and clinical evaluation of the harmonic scalpel in thoracic surgery; Kurume Med J; vol. 46; No. 1; pp. 25-29; 1999.
Hefni et al.; Safety and efficacy of using the ligasure vessel sealing system for securing the pedicles in vaginal hysterectomy: randomized controlled trial; BJOG; vol. 112; No. 3; pp. 329-333; Mar. 2005.
Heniford et al.; Initial results with an electrothermal bipolar vessel sealer; Surg Endosc; vol. 15; No. 8; pp. 799-801; Aug. 2001.
Johnson & Johnson Gateway, LLC; The Gynecare Versapoint (Product Information); http://jnjgateway.com/home/jhtml?loc=USENG&page=viewContent&id=edea000100001747&parentid=fc0de00100000334; downloaded Oct. 20, 2005.
Kamat et al.; Superiority of electrocautery over the suture method for achieving cervical cone bed hemostasis; Obstet Gynecol; vol. 102; No. 4; pp. 726-730; Oct. 2003.
Kennedy et al.; High-burst-strength, feedback-controlled bipolar vessel sealing; Surg Endosc; vol. 12; No. 6; pp. 876-878; Jun. 1998.
Kim et al.; Design and fabrication of a locomotive mechanism for capsule-type endoscopes using shape memory alloys (SMAs); IEEE/ASME Trans on Mechatronics; vol. 10; No. 1; pp. 77-86; Feb. 2005.
Kovac; Transvaginal hysterectomy: rationale and surgical approach; Obstet. Gynecol.; vol. 103; pp. 1321-1325; 2004.
Landman et al.; Evaluation of a vessel sealing system, bipolar electrosurgery, harmonic scalpel, . . . in a porcine model; J. urol; vol. 169; No. 2; pp. 697-700; Feb. 2003.
Levy, et al.; Update on hysterectomy: new technology and techniques; A Supp. to OBG Maganagement; Feb. 2003.
Levy, et al.; Use of a new vessel ligation device during vaginal hysterectomy (presentation abstract); presented at FIGO 2000; Washington, D.C.; 2000.
Lin et al.; Application of ultrasonic scalpel in gynecologic operative laparoscopy; Chin Med J (Engl.); vol. 114; No. 12; pp. 1283-1285; Dec. 2001.
Live Tissue Connect Technologies; company profile; (http://www.onemedplace.com/database/compdisplay_print.php?CompanyID=11508); 1 pg.; Oct. 19, 2010 (downloaded Feb. 7, 2011).
Lyons et al.; An innovative bipolar instrument for laparoscopic surgery; JSLS; vol. 9; No. 1; pp. 39-41; Jan.-Mar. 2005.
McClurken et al.; Collagen shrinkage and vessel sealing; Technical brief #300. Dover, NH: Tissue Link Medical; 2001.

Nojarov et al.; High-energy scissors mode; Phys Rev C Nucl Phys; vol. 51; No. 5; pp. 2449-2456; 1995 (http://arxiv.orgiabs/nucl-th/9502001v1).

Parikh et al.; Three dimensional virtual reality model of the normal female pelvic floor; Annals of Bimedical Engineering; vol. 32; pp. 292-296; Feb. 2004.

Refractec, Inc.; Medical use of radiofrequency (RF) energy; (http://www.locateadoc.com/Site_Tools/Print.cfm); 2 pgs.; Aug. 23, 2008 (downloaded Feb. 7, 2011).

SAGES 2001 Hands-On Course I—Taking it the next level: advanced laparoscopic techniques; http://vvww.sages.org/01program/syllabi/ho1/ho1.html#schirme; 24 pgs.; downloaded Oct. 5, 2005.

SAGES 2001 Nurses Program, Session 1; http://sages.org/01program/syllabi/nurse/nurse.html; downloaded Jan. 24, 2011; 5 pgs.

Srisombut et al.; Laparoscopic hysterectomy using laparoscopic coagulating shears: experience of 15 cases; J. Med Assoc Thai; vol. 83; No. 8; pp. 915-920; Aug. 2000.

SURGRX 510(K) Summary (# K031133), Palo Alto, CA; 5 pgs.; Jul. 3, 2003.

TREAT; A new thermal device for sealing and dividing blood vessels; http://www.starioninstruments.com/PDFs/Treat.pdf; downloaded Jun. 29, 2005; 2 pgs.

Tyco Healthcare; The LigaSure Vessel Sealing System (Brochure); Apr. 2002; 8 pgs.

Valleylab Products; Valleylab Products—Electrosurgical Forceps: The surgeon's choice for quality and precision (product information); http://www.valleylab.com/product/es/accessories/forceps_over.html; downloaded Oct. 20, 2005.

Valleylab Products; Valleylab Products—Ligasure} vessel sealing system (product information); http://www.valleylab.com/product/vessel_seal/index.html; downloaded Oct. 20, 2005.

Kerver et al.; U.S. Appl. No. 13/070,391 entitled "Articulable electrosurgical instrument with a stabilizable articulation actuator," filed Mar. 23, 2011.

Van Lue et al.; U.S. Appl. No. 13/110,848 entitled "Electrosurgical tissue sealing augmented with a seal-enhancing composition," filed May 18, 2011.

* cited by examiner

IMPEDANCE MEDIATED POWER DELIVERY FOR ELECTROSURGERY

BACKGROUND OF THE INVENTION

1. Technical Field

The invention relates to electrosurgery. More particularly, the invention relates to impedance mediated power delivery for electrosurgery.

2. Description of the Prior Art

The state of the art of electrosurgery is well summarized in U.S. patent publication no. 2009/0157071 (Wham et al), where it is stated:

"Electrosurgery involves application of high radio frequency electrical current to a surgical site to cut, ablate, or coagulate tissue. In monopolar electrosurgery, a source or active electrode delivers radio frequency energy from the electrosurgical generator to the tissue and a return electrode (e.g., a return pad) carries the current back to the generator. In monopolar electrosurgery, the source electrode is typically part of the surgical instrument held by the surgeon and applied to the tissue to be treated. The patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact of body tissue with either of the separated electrodes does not cause current to flow.

Bipolar electrosurgery generally involves the use of forceps. A forceps is a pliers-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize mechanical clamping action and electrical energy to effect hemostasis on the clamped tissue. The forceps include electrosurgical conductive plates which apply the electrosurgical energy to the clamped tissue. By controlling the intensity, frequency and duration of the electrosurgical energy applied through the conductive plates to the tissue, the surgeon can coagulate, cauterize and/or seal tissue.

Tissue or vessel sealing is a process of liquefying collagen, elastin and ground substances in tissue so that they reform into a fused mass with significantly-reduced demarcation between opposing tissue structures. Cauterization involves the use of heat to destroy tissue and coagulation is a process of desiccating tissue wherein the tissue cells are ruptured and dried.

Tissue sealing procedures involve more than simply cauterizing or coagulating tissue to create an effective seal; the procedures involve precise control of a variety of factors. For example, in order to affect a proper seal in vessels or tissue, it has been determined that two predominant mechanical parameters must be accurately controlled: the pressure applied to the tissue; and the gap distance between the electrodes (i.e., distance between opposing jaw members or opposing sealing plates). In addition, electrosurgical energy must be applied to the tissue under controlled conditions to ensure creation of an effective vessel seal. Techniques have been developed whereby the energy applied to the tissue is varied during the tissue sealing process to achieve a desired tissue impedance trajectory. When a target tissue impedance threshold is reached, the tissue seal is deemed completed and the delivery of electrosurgical energy is halted."

Wham et al takes the approach of incorporating a cooling period subsequent to a tissue reaction that occurs after the application of electrosurgical energy to the tissue, where such electrosurgical energy is applied to the tissue in accordance with an algorithm that reduces power with increasing tissue impedance (see Wham et al, FIG. 8). However, this approach merely adjusts the amount of electrosurgical energy applied as it tracks tissue impedance vis a vis a target tissue impedance. The approach does not take in to account the actual change of state within the tissue and thus does not address such issues as thermal damage to the tissue and defective sealing.

SUMMARY OF THE INVENTION

An embodiment of the invention provides an electrosurgical technique that addresses such issues as thermal damage to the tissue, partial coverage of the electrodes of the electrosurgical device by tissue, thin tissue, and defective sealing. This improvement is accomplished by use of an adaptive algorithm that monitors, inter alia, the rate of tissue impedance change. An aspect of the invention thus examines impedance levels achieved within a specific timeframe to determine an impedance ramp and/or slope rate, which indicates the rate at which the target tissue is undergoing a phase or state change and, thus, indicates tissue processing. The level of electrosurgical energy applied to the target tissue is adjusted in real time in accordance with such rate of impedance change. This approach, in effect, applies the energy at levels that allow tissue phase or state change to occur in an optimum fashion, for example allowing moisture to escape from the tissue slowly, and thus avoid thermal damage. As a result, such undesired results as thermal damage and defective sealing are mitigated.

Another embodiment of the invention determines impedance achieved within a specific interval and adjusts the electrosurgical energy applied to the tissue after a threshold impedance has been maintained or exceeded for a predetermined interval.

DETAILED DESCRIPTION OF THE INVENTION

An embodiment of the invention provides an electrosurgical technique that addresses such issues as thermal damage to the tissue, partial coverage of the electrodes of the electrosurgical device by tissue, thin tissue, and defective sealing. This improvement is accomplished by use of an adaptive algorithm that monitors, inter alia, the rate of tissue impedance change. An aspect of the invention thus examines impedance levels achieved within a specific timeframe to determine an impedance ramp and/or slope rate, which indicates the rate at which the target tissue is undergoing a phase or state change and, thus, indicates a desired rate of tissue processing. The level of electrosurgical energy applied to the target tissue is adjusted in real time in accordance with such rate of impedance change and/or impedance thresholds reached. This approach, in effect, applies the energy at levels that allow tissue phase or state change to occur in an optimum fashion, for example allowing moisture to escape from the tissue slowly avoiding thermal damage and/or reducing energy for thin tissue or partially covered electrodes. As a result, such undesired results as thermal damage and defective sealing are mitigated.

Another embodiment of the invention determines impedance achieved within a specific interval and adjusts the electrosurgical energy applied to the tissue after a threshold impedance has been exceeded for a predetermined interval. This approach, in effect, determines when the tissue phase or state change has successfully occurred and that the application of energy can be halted.

Figure 1:
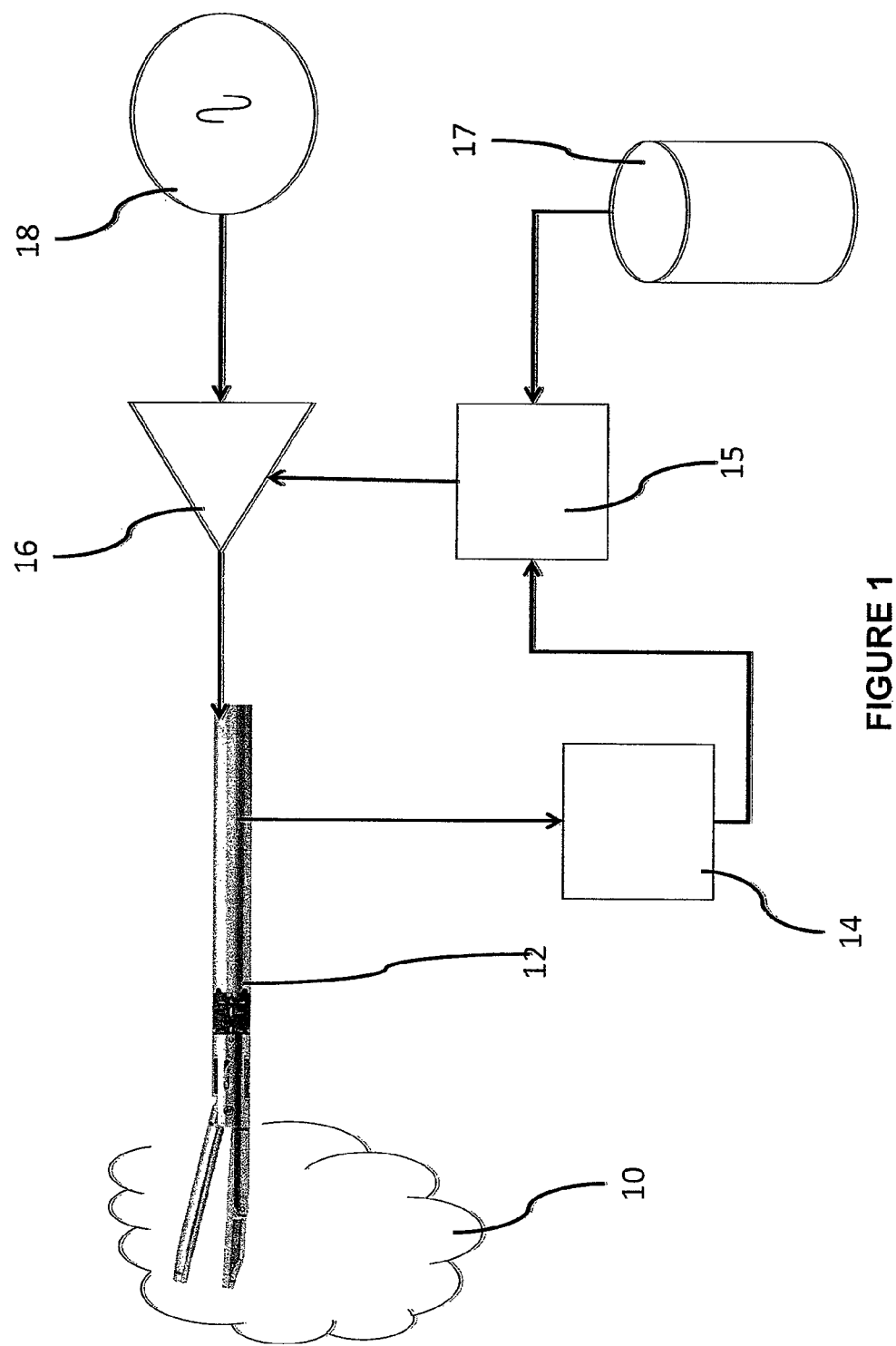
FIG. 1 is a block schematic diagram of an apparatus for impedance mediated power delivery for microsurgery according to the invention.

FIG. 1 is a block schematic diagram of an apparatus for impedance mediated power delivery for microsurgery according to the invention. In FIG. 1, an individual is shown undergoing a procedure in which electrosurgery is being performed on the individual's tissue 10 by an electrosurgical appliance 12, as is known in the art. A source of energy, such as an RF generator 18 is coupled to the electrosurgical appliance by a control circuit 16. The control circuit is operable to adjust any of the current and voltage output and, in some embodiments, adjust the phase relation between the voltage and current, from the RF generator and, thus, to adjust the power output of the RF generator. The control circuit can adjust the RF generator output up and/or down in steps and/or in a selected ramp and/or slope.

The effect of the electrosurgical appliance on the tissue is monitored at the site of tissue treatment by one or more sensors within or proximate to the electrosurgical appliance. A signal produced by the one or more sensors is coupled to a sensor circuit 14. The sensors can monitor such factors as temperature, impedance, RF voltage, RF current, and the like. In the preferred embodiment, the sensor monitors the components of impedance and RF power.

The sensor circuit generates an output signal that is coupled to a processor 15. The processor operates under control of a program and adjusts the output of the RF generator by issuing control signals to the control circuit. In doing so, the processor applies the signal provided by the sensor circuit to the program and adjusts the RF power supplied to the tissue, for example, in real time in response to signal generation by the sensors. Thus, in some embodiments of the invention the process of treating the tissue is monitored in real time and the effect of the treatment upon the tissue, as indicated by the sensors, is used to mediate the application of energy to the tissue. The program may be retained in a memory 17 and includes both instructions for operating the processor and parameters that determine how to respond to signals from the sensor, timing information, and the like.

An important feature of the invention is the manner in which the processor operates the control circuit and, thus, the manner in which energy is supplied to the tissue, in response to signals provided to the processor from the one or more sensors via the sensor circuit. In a preferred embodiment, the one or more sensors monitor the impedance of the tissue. As the tissue is processed by application of energy thereto, a phase or state change gradually occurs and this phase or state change results in a change in the impedance of the tissue. It is known in the art to monitor tissue impedance in connection with such treatments. Uniquely, an embodiment of the invention provides an adaptive power ramp and/or slope by which a lower level of energy is initially supplied to the tissue. The output of the RF generator supplied to the tissue is gradually increased to a higher level of energy and/or the rate of power output is increased or decreased. This ramp and/or slope is provided for a predetermined interval. In some embodiments, during the interval, the impedance of the tissue is monitored in real time and the change in impedance over time and/or threshold achieved is used to determine the slope or rate of a next ramp. The change in impedance is thought to indicate the rate at which tissue phase or state change is progressing. If the rate of such change occurs too quickly, the tissue may be degraded as a result of thermal damage, for example where moisture in the tissue escapes too quickly or forcefully in the form of steam. Thus, key to the invention is a recognition that the rate of change of impedance tracks the rate of phase or state change of the tissue. The processor is programmed to adjust the energy ramp and/or slope during each interval of energy application based upon this rate of change in impedance over time and/or by impedance thresholds achieved. It should be appreciated that, for purpose of the discussion herein, the ramp of energy output refers to the difference between the output level at the start of the ramp and the output level achieved at the end of the ramp, while the slope refers to the rate at which the energy output is increased over time.

One aspect of the invention allows a determination to be made if the electrosurgical appliance electrodes are partially covered by the tissue that is being treated, or if the tissue that is being treated is relatively thin, such as 0.5 mm or less. If the electrodes are partially covered by the tissue or if thinner tissue is being treated, the rate of change of impedance is greater because less tissue is being treated. Accordingly, the energy supplied or the interval over which energy is supplied can be adjusted. For example, in some embodiments, if the partial coverage of tissue or if thinner tissue is being treated, the energy ramp and/or slope is more gradual, whereas if the tissue is thick, then the rate of change of impedance is lesser, and the energy ramp and/or slope is steeper. Other embodiments adjust the power level and/or interval over which power is delivered to the tissue in accordance with, for example, rate of change of tissue impedance. In this way, the invention applies the rate of change in impedance and/or threshold levels achieved, to mediate energy supplied to the tissue.

In an alternate or supplemental embodiment, a target tissue impedance is established, based upon criteria stored in the memory and, once that impedance is reached, energy continues to be supplied for a predetermined interval. That is, a target tissue impedance is achieved and energy is supplied to the tissue for a period of time after the impedance is reached. This embodiment of the invention determines a preferred tissue impedance for processing and then continues supplying energy to the tissue once this impedance is reached. This is accomplished by a ramp and/or slope mechanism similar to that described above, where a measure of sustained energy is maintained at a particular impedance. When a certain time has elapsed at this threshold impedance, tissue processing is considered complete.

The two embodiments of the invention may be used alone or in combination. For example, the rate of change in impedance may be used to determine when sufficient tissue processing has occurred, that is when a threshold impedance is reached; and the threshold impedance may then be used to continue processing until the tissue is completely transformed. In this way, the tissue is processed at a rate that avoids thermal damage and defective sealing, and the tissue is processed sufficiently to complete phase or state change.

Figure 2:
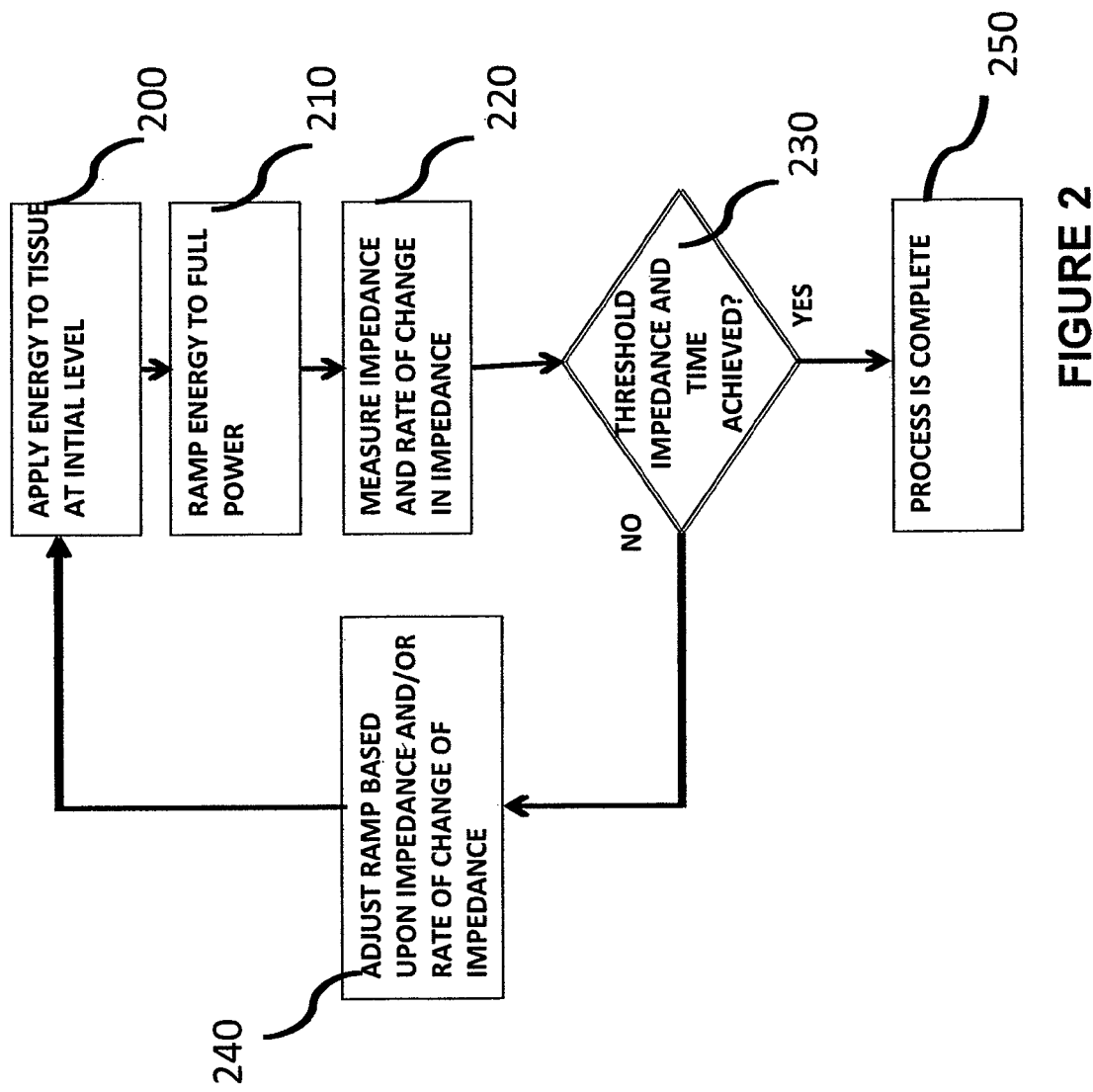
FIG. 2 is a flow diagram showing an algorithm for impedance mediated power delivery for microsurgery according to a first embodiment of the invention.

FIG. 2 is a flow diagram showing an algorithm for impedance mediated power delivery for microsurgery according to a first embodiment of the invention. In FIG. 2, energy is applied to the tissue at an initial level (200) to begin tissue processing in a gentle fashion. The energy level is ramped to a full energy level (210) in accordance with a ramp and slope that is established as a function of rate of change of impedance (220). If a threshold impedance is reached and maintained or exceeded over a predetermined amount of time, indicating that the tissue is fully processed (230), the process is complete (250) and energy is no longer supplied to the tissue. Else, the energy ramp is adjusted based upon the tissue impedance and the rate of change in the tissue impedance (240) and the process continues.

Figure 3:
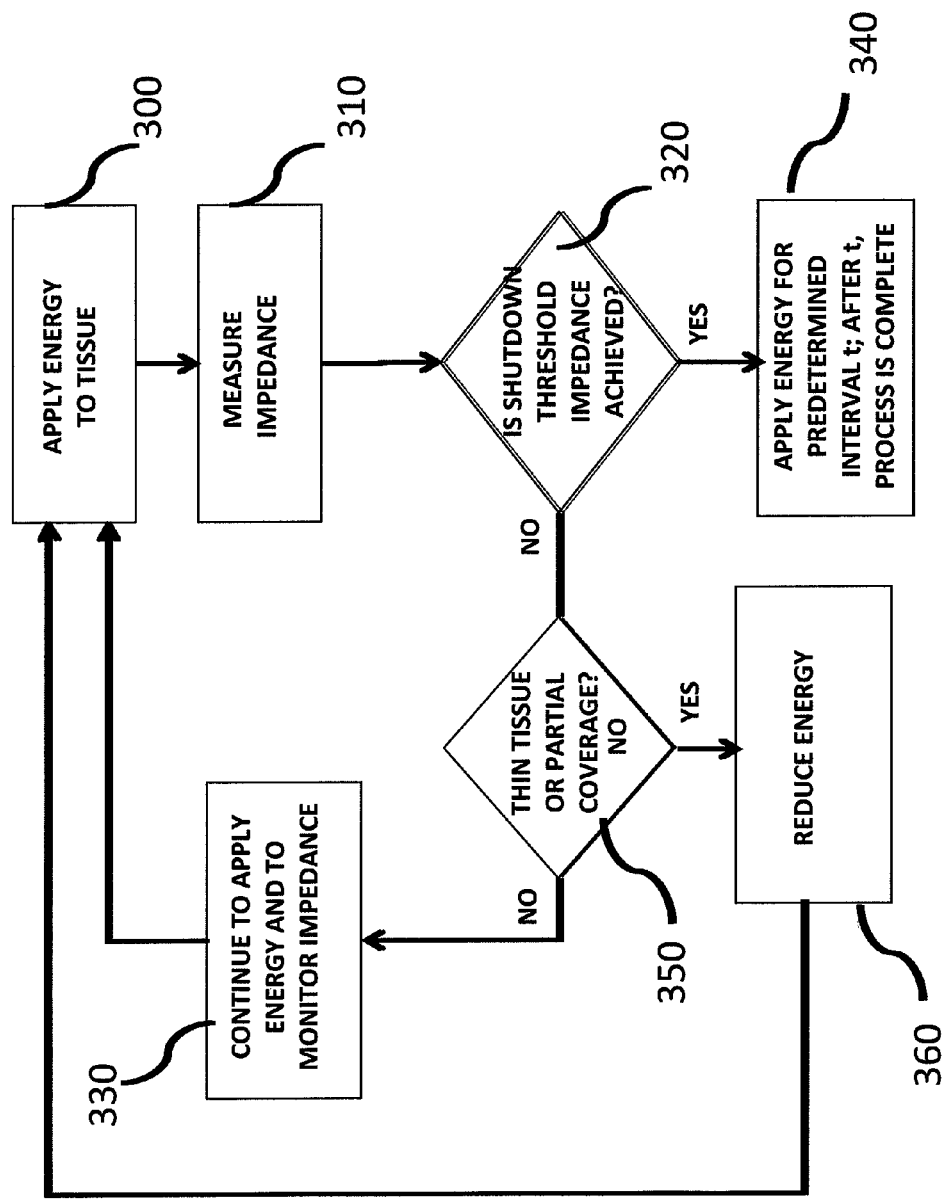
FIG. 3 is a flow diagram showing an algorithm for impedance mediated power delivery for microsurgery according to a second embodiment of the invention.

FIG. 3 is a flow diagram showing an algorithm for impedance mediated power delivery for microsurgery according to a second embodiment of the invention. In FIG. 3, energy is applied to the tissue (300) and the tissue impedance is measured (310). If the threshold impedance is achieved, e.g. 250 Ohms (320), then energy is applied to the tissue for a predetermined, cumulative interval t, e.g. 1.5 seconds. At the end of this interval, tissue processing in complete (340). If the threshold impedance is not achieved, the tissue impedance is monitored as energy is applied to the tissue (330) and the process continues. Further, if thin tissue or partial tissue coverage is detected (350), then the energy level is reduced, e.g. voltage is reduced by 75% (350), and the process then continues as outlined above.

As discussed above, both techniques may be combined. For example, the application of energy in the embodiment of FIG. 3 may be in accordance with a ramp and/or slope that is determined as a function of the rate of change of the tissue impedance and/or an impedance threshold achieved. Likewise, the interval of energy application to the tissue in the embodiment of FIG. 2 may be in accordance with the determination of a threshold impedance, that is the ramp may be eliminated once the threshold impedance is achieved, at which point energy is supplied to the tissue at a higher level.

Figure 4:
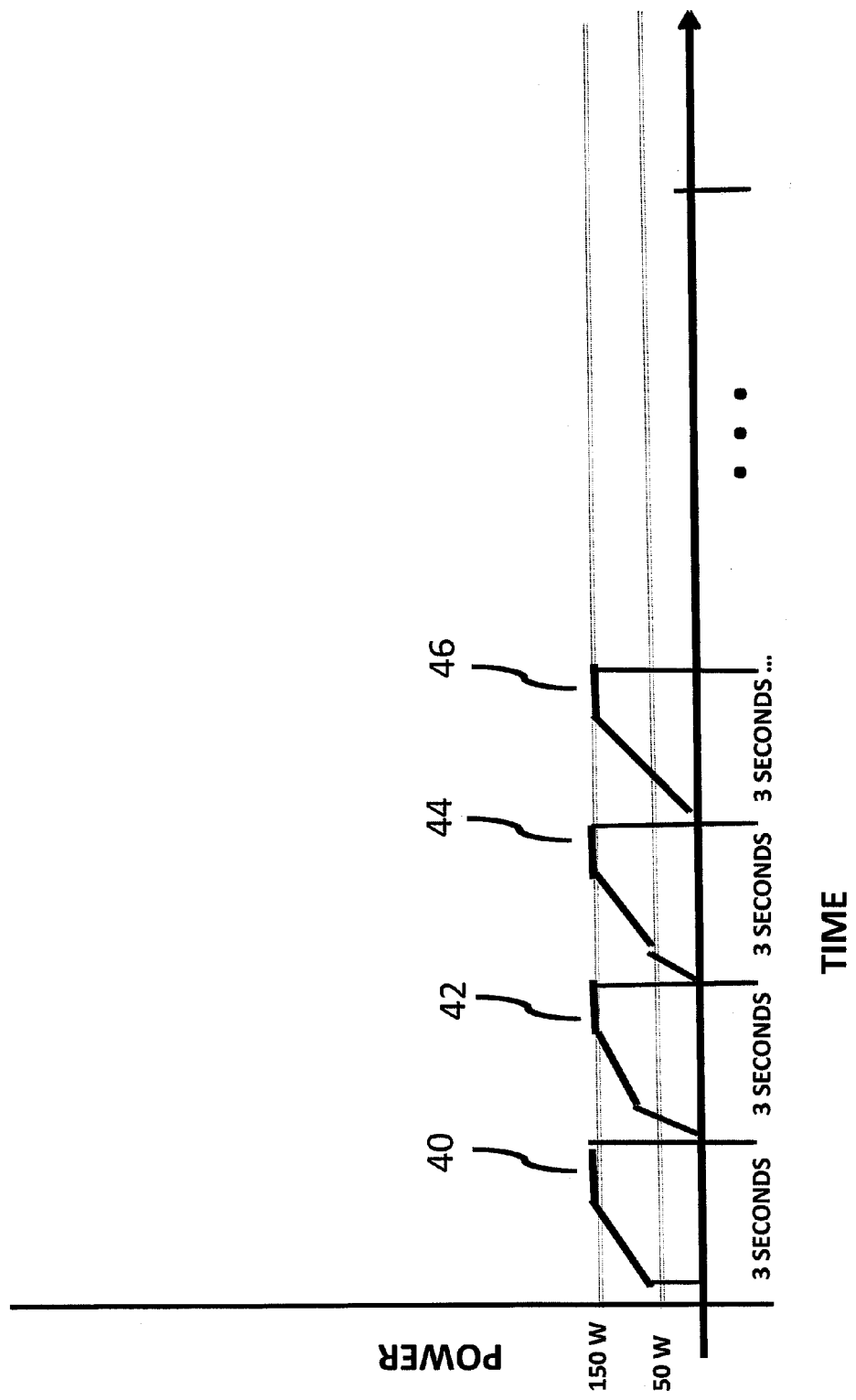
FIG. 4 is a timing diagram showing an impedance mediated power delivery ramp for microsurgery according to the invention.

FIG. 4 is a timing diagram showing an impedance mediated power delivery ramp for microsurgery according to the invention. In FIG. 4, a first ramp 40 is shown over an interval of three seconds. For purpose of this embodiment of the invention, the ramp interval is three seconds and the same interval is used for each ramp. Those skilled in the art will appreciate that other intervals may be used and that the intervals themselves may be varied as a result of the rate of impedance change.

It can be seen that the slope of the first ramp interval includes a first, steep portion, a shallow middle portion, and a relatively flat third portion. Thereafter, the energy is reduced and the next ramp is commenced. In this embodiment, each ramp is mediated in real time in view of the rate of change of tissue impedance, and can also include the absolute impedance (as in the embodiment of FIG. 3) as well. The slope of the second ramp 42 includes less of a steep, initial portion; the slope of the third ramp 44 has a less pronounced slope; the slope of the fourth ramp 46 has an even shallower slope. The area under each ramp indicates the total energy supplied to the tissue during the ramp. In the preferred embodiment, as the tissue is processed and less moisture is retained in the tissue, the energy can be applied at a greater rate, thus reducing sealing time. Thus, as the tissue is processed in this embodiment, more energy is supplied to the tissue, i.e. the ramp is increased, and the energy is supplied more quickly, i.e. the slope is increased. In other embodiments, either or both of the slope and ramp may be increased or decreased at the same time; one of the slope or ramp may be held constant, while the other of the slope or ramp is increased or decreased; one of the slope or ramp may be increased, while the other of the slope or ramp is increased; or the relative increase and/or decrease of the slope and/or ramp may be altered over time, all in accordance with the rate of phase or state change in the tissue. In this way, the rate of phase or state change in the tissue, as indicated by the rate of change of tissue impedance, is used to mediate the delivery of energy to the tissue.

Figure 5:
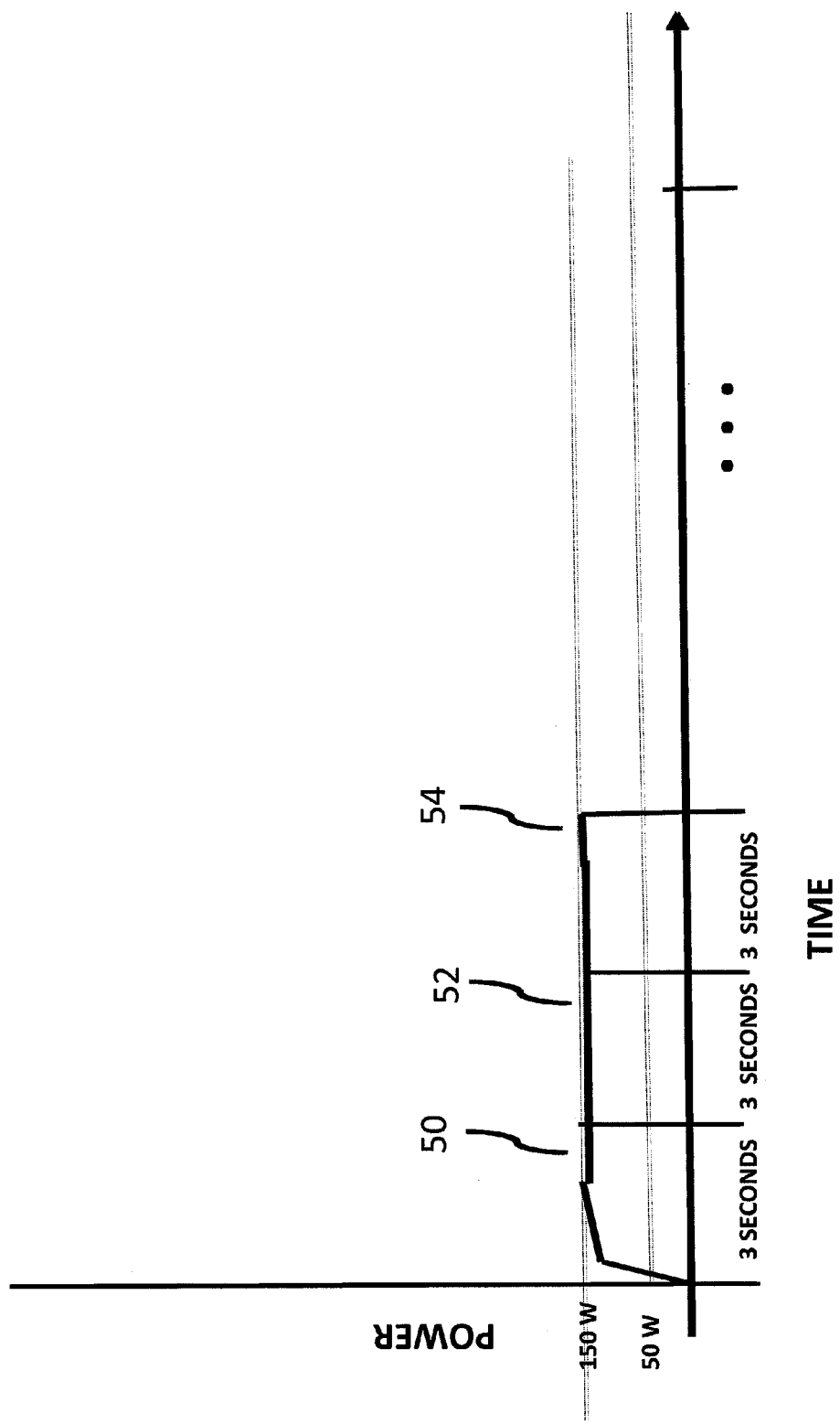
FIG. 5 is a timing diagram showing an impedance mediated power delivery interval for microsurgery according to the invention.

FIG. 5 is a timing diagram showing an impedance mediated power delivery interval for microsurgery according to the invention. In FIG. 5, an initial energy ramp 50 is supplied to the tissue. A subsequent ramp need not be provided in this embodiment. Once the desired impedance is reached, the energy supplied to the tissue 52/54 is maintained at a desired level for a predetermined interval of time.

EXAMPLES

Modified Power Delivery (Mitigation for Thermal Spread)

Figure 6:
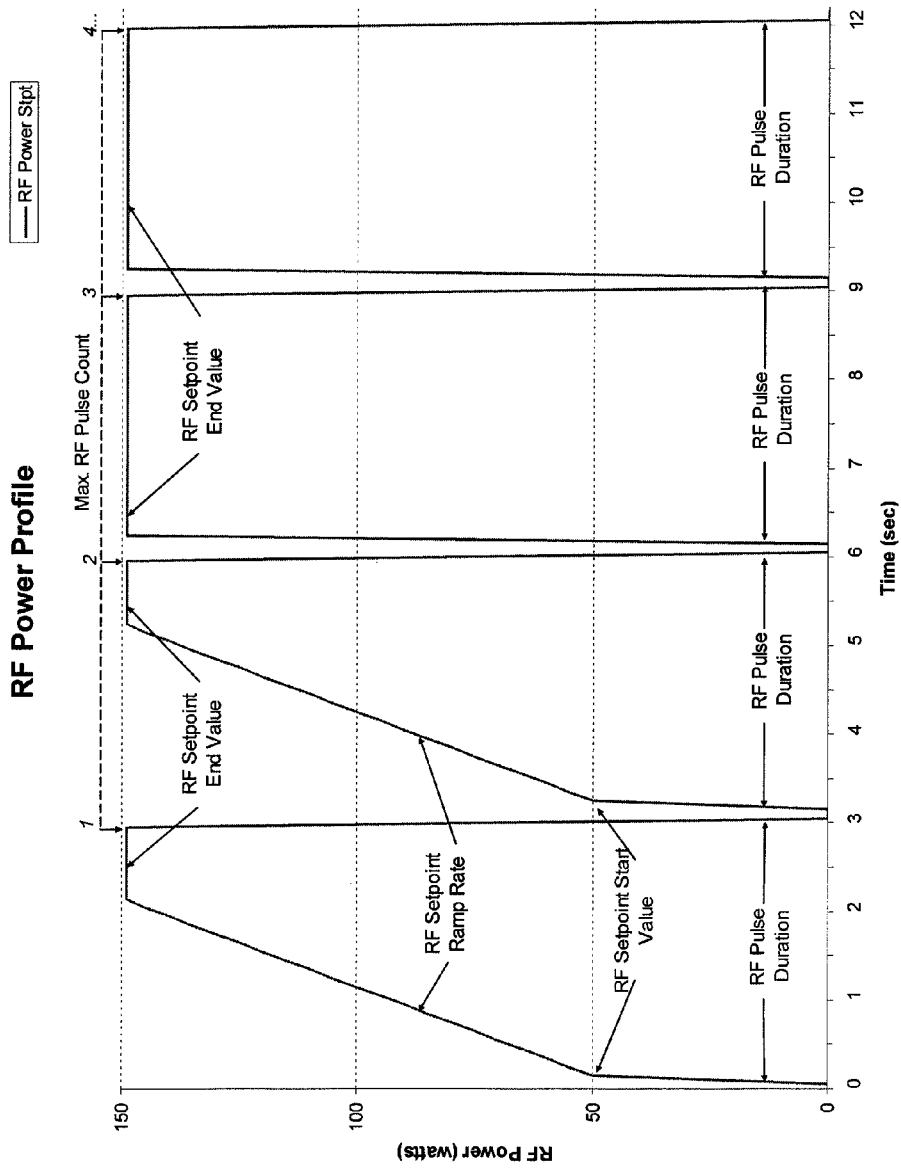
FIG. 6 is a timing diagram showing a modified power delivery profile according to the invention.

RF energy is delivered to the target tissue in multiple pulses of energy. The length of each pulse is defined as the RF Pulse Duration and the maximum number of pulses allowed for each seal is defined as the Max. RF Pulse Count. See FIG. 6.

Method:

1. The first RF pulse for a seal starts at a power level defined as the RF Setpoint Start Value. See FIG. 6.

2. The RF power level is then increased from the RF Setpoint Start Value by a rate defined as the RF Setpoint Ramp and/or slope rate until the power level reaches the upper level defined as the RF Setpoint End Value. The RE power level remains at this value until the end of the pulse time is reached. See FIG. 6.

Figure 7:
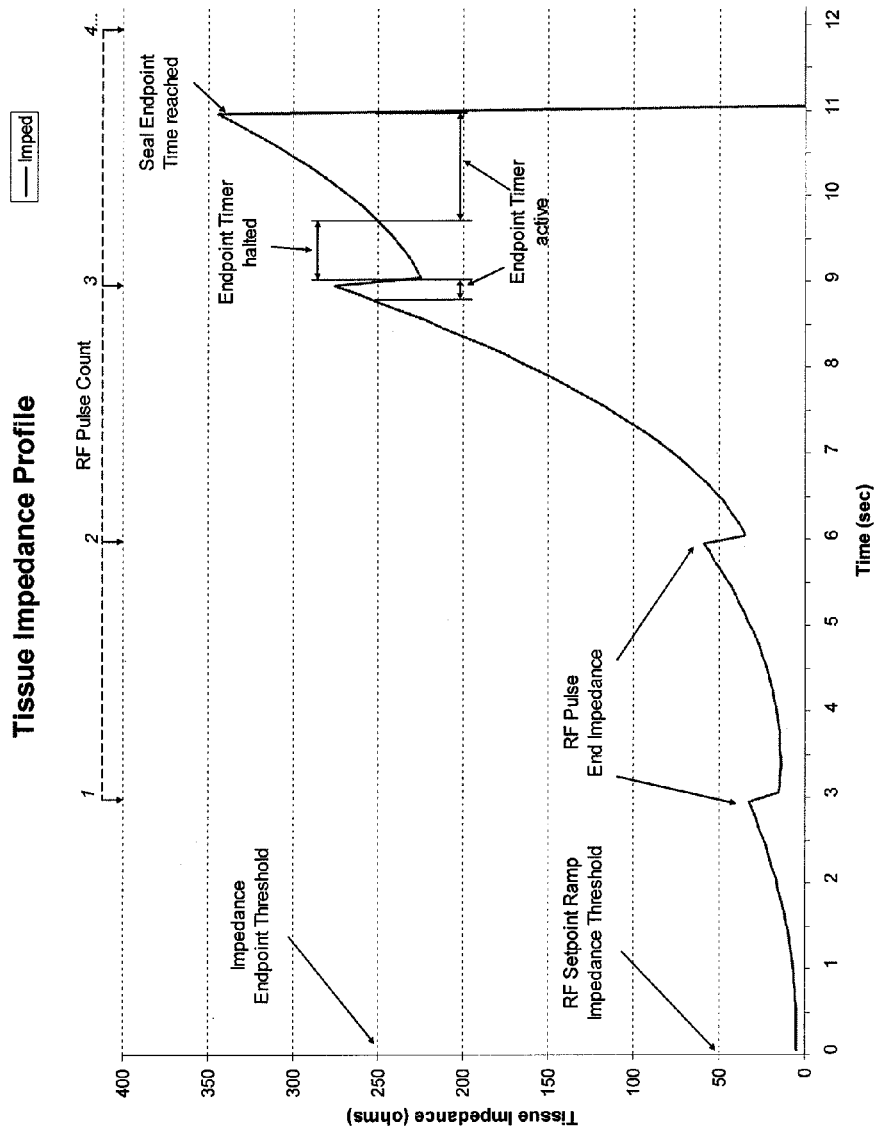
FIG. 7 is a timing diagram showing an endpoint detection profile according to the invention.

3. At the end of each pulse, the tissue impedance value is calculated and recorded as the RF Pulse End Impedance and the power levels are then set to zero. See FIGS. 6 and 7.

4. For all pulses subsequent to the first, the following evaluations are made. See FIGS. 6 and 7:

If the RF Pulse End Impedance is less than a threshold defined as RF Setpoint Ramp Impedance Threshold, the RF power delivered is ramped identical to the first pulse.

If the RF Pulse End Impedance is greater than the RF Setpoint Ramp Impedance Threshold, the RF power delivered is not ramped but stepped directly to the RF Setpoint End Value.

TABLE 1

Typical Values and Ranges - Modified Power Delivery

| Value | Typical | Range |
|---|---|---|
| RF Pulse Duration | 3.0 sec. | 0.5-10.0 sec. |
| Max. RF Pulse Count | 5 pulses | 1-30 pulses |
| RF Setpoint Start Value | 50 watts | 25-150 watt |
| RF Setpoint Ramp and/or slope rate | 50 watt/sec. | 1-100 watt/sec. |

TABLE 1-continued

Typical Values and Ranges - Modified Power Delivery

| Value | Typical | Range |
|---|---|---|
| RF Setpoint End Value | 150 watts | 50-150 watt |
| RF Pulse End Impedance | based on tissue response | 2-900 ohms |
| RF Setpoint Ramp Impedance Threshold | 50 ohms | 5-250 ohms |

Endpoint Detection

The sealing cycle is terminated when the tissue impedance reaches a predetermined threshold for a specified length of time OR when a fault or error condition is detected. A successful sealing cycle is defined here.

Method:

1. The tissue impedance is calculated using the signals from the RF monitoring hardware circuits.

2. When the calculated tissue impedance exceeds a threshold level defined as the Impedance Endpoint Threshold, a timer is started. If the calculated tissue impedance falls below the Impedance Endpoint Threshold, the timer is halted. See FIG. 7.

3. If the above timer accumulates a value defined as the Seal Endpoint Time, the RF delivery is halted, the user is notified of the completed seal and the system is placed in the Ready state. See FIG. 7.

TABLE 2

Typical Values and Ranges - Endpoint Detection

| Value | Typical | Range |
|---|---|---|
| Impedance Endpoint Threshold | 250 ohms | 100-750 ohms |
| Seal Endpoint Time | 1.5 sec. | 0.1-5.0 secs. |

Partial Coverage Mitigation

The exemplary RF generator should seal tissue that is fully covered by the RF electrodes, as well as smaller tissue that is partially covered by the RF electrodes. Partially covered electrodes can create a challenge to RF delivery due to the increased rate at which the tissue desiccates. The following describes the mitigation incorporated in the RF delivery algorithm to address this issue.

Method:

1. The tissue impedance is calculated using the signals from the RF monitoring hardware circuits.

Figure 8:
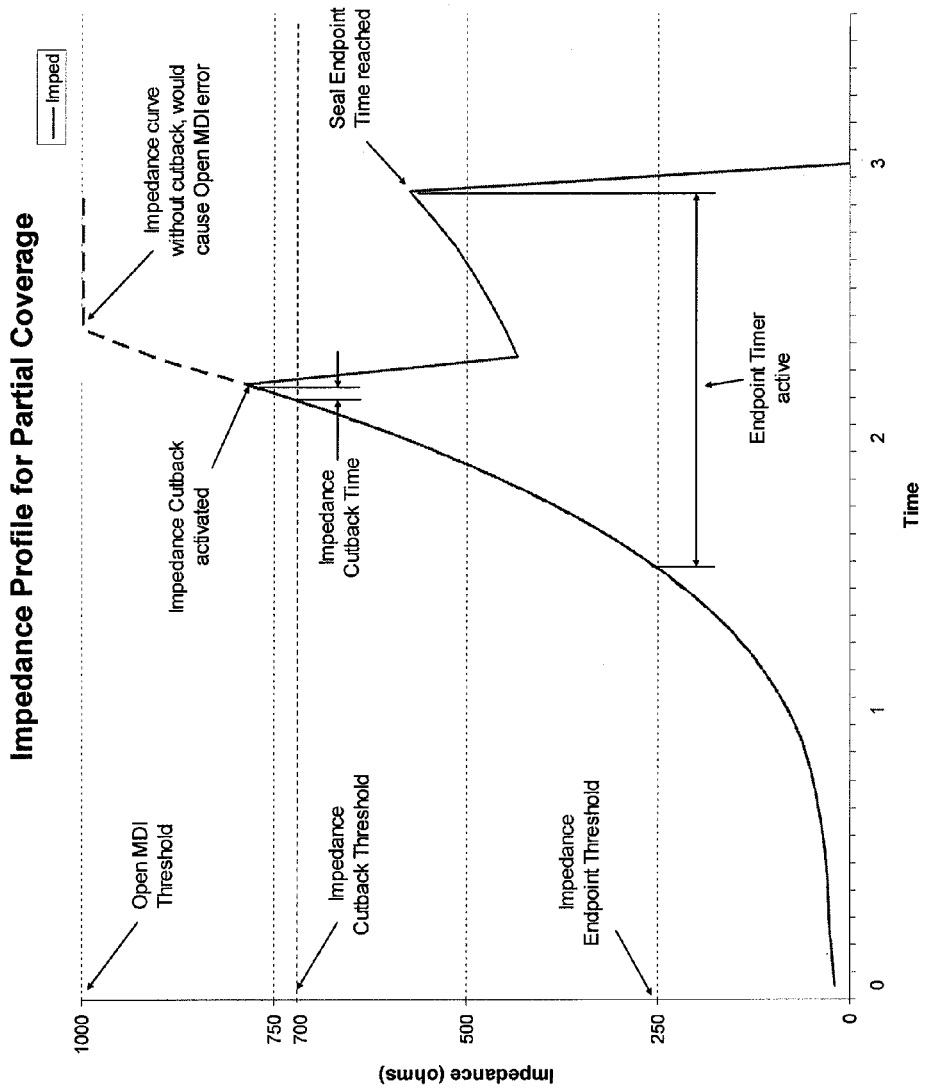
FIG. 8 is a timing diagram showing a partial tissue coverage mitigation profile according to the invention.

2. When the calculated tissue impedance exceeds a threshold level defined as the Impedance Cutback Threshold for a duration defined as the Impedance Cutback Time, the RF delivery is reduced by decreasing the RF Voltage being delivered. See FIG. 8.

3. The RF Voltage is reduced by a value defined as RF Voltage Cutback.

4. If the tissue impedance exceeds the Impedance Cutback Threshold a second time, the RF Voltage is reduced again by the value of the RF Voltage Cutback.

TABLE 3

Typical Values and Ranges - Partial coverage Mitigation

| Value | Typical | Range |
|---|---|---|
| Impedance Cutback Threshold | 700 ohms | 100-900 ohms |
| Impedance Cutback Time | 0.1 sec. | 0.01-2.0 secs. |
| RF Voltage Cutback | 35 volts | 1-100 volts |

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

The invention claimed is:

1. An electrosurgery method, comprising the steps of:
   applying energy to an individual's tissue with an electrosurgical appliance that comprises a plurality of electrosurgical appliance electrodes;
   monitoring rate of tissue impedance change;
   generating a signal indicative of said rate of tissue impedance change;
   providing a processor configured to determine an impedance ramp and/or slope rate from said signal, said impedance ramp and/or slope rate indicates a rate at which said individual's tissue is undergoing a phase or state change;
   said processor configured to continuously adjust a ramp and/or slope of energy applied to said individual's tissue via said electrosurgical appliance in real time, and to adjust a rate at which an ultimate level of energy is achieved while applying energy to said individual's tissue in accordance with said impedance ramp and/or slope rate; and
   continuing to monitor said rate of tissue impedance change and to adjust said level of energy applied to said individual's tissue until tissue processing is complete;
   wherein energy is applied to said individual's tissue at levels that allow tissue phase or state change to occur in an optimum fashion,
   wherein a first radiofrequency, RF, pulse for a seal starts at a power level defined as start value,
   the RF power level is then increased from the start value until the power level reaches an upper level and the RF power level remains at this upper level until the end of the pulse time is reached,
   at the end of each pulse, the tissue impedance value is calculated and recorded as an RF Pulse End Impedance, and the power levels are then set to zero,
   for all pulses subsequent to the first, the following evaluations are made,
   if the RF Pulse End Impedance is less than a threshold, the RF power delivered is ramped similar to the first pulse, and
   if the RF Pulse End Impedance is greater than said threshold, the RF power delivered is not ramped but stepped directly to said upper level.

2. The method of claim 1, further comprising the step of:
   applying energy to said individual's tissue at an initial energy level and increasing said energy level to a terminal energy level.

3. The method of claim 2, further comprising the step of:
   increasing said energy level from said initial energy level to said terminal energy level in any of a series of discrete steps or in a continuous fashion over time.

4. The method of claim 1, further comprising the steps of:
   monitoring tissue impedance;
   generating a signal indicative of said tissue impedance;
   providing a processor configured to determine when a threshold impedance is reached within a specific interval;
   said processor configured to apply a constant, predetermined level of energy to said individual's tissue after said threshold impedance is reached and to continue application of said constant, predetermined level of energy to said individual's tissue for a predetermined interval; and said processor configured to discontinue application of energy to said individual's tissue after completion of said predetermined interval.

5. The method of claim 1, further comprising the step of:

providing a processor configured to determine if said electrosurgical appliance electrodes are partially covered by the individual's tissue or are covered by thin tissue by determining if a rate of change and/or impedance threshold is reached, and thereafter applying a decreasing ramp rate and/or power cutback to prevent over-processing of the tissue.

6. An electrosurgery method, comprising the steps of:

applying energy to an individual's tissue with an electrosurgical appliance;

monitoring tissue impedance;

generating a signal indicative of said tissue impedance;

providing a processor configured to determine when a threshold impedance is reached within a specific interval;

said processor configured to apply a constant, predetermined level of energy to said individual's tissue after said threshold impedance is reached and to continue application of said constant, predetermined level of energy to said individual's tissue for a predetermined interval; and said processor configured to discontinue application of energy to said individual's tissue after completion of said predetermined interval, wherein an impedance mediated power delivery ramp for microsurgery is provided, a slope of said power delivery ramp of a first ramp interval including a first, steep portion, a shallow middle portion, and a relatively flat third portion, whereafter, the energy is reduced and a second ramp is commenced wherein each ramp is mediated in real time in view of the rate of change of tissue impedance, the slope of said second ramp includes less of a steep, initial portion, wherein, as the tissue is processed, more energy is supplied to the tissue, i.e. the ramp is increased.

7. The method of claim 6, wherein said step of providing a processor configured to determine when a threshold impedance is reached within a specific interval comprises the step of providing a processor configured to:

determine when each of a plurality of threshold impedances is reached within a corresponding specific interval; and discontinue application of energy to said individual's tissue after completion of a last of said corresponding predetermined intervals.

8. An electrosurgery apparatus, comprising:

an electrosurgical appliance for performing electrosurgery on an individual's tissue;

a source of energy coupled to the electrosurgical appliance by a control circuit, said control circuit configured to adjust any of the current and voltage output from said source of energy and, thus, to adjust power output of said source of energy, said control circuit configured to adjust said power output of said source of energy up and/or down in steps and/or in a selected ramp;

a sensor within or proximate to said electrosurgical appliance for monitoring an effect of said electrosurgical appliance on said individual's tissue and producing a tissue impedance signal therefrom;

a processor coupled to receive said tissue impedance signal from said sensor;

said processor operating under control of a program stored in a memory, said processor configured to adjust the output of said source of energy by issuing control signals to said source of energy, said processor configured to apply the signal from said sensor to said program and to adjust the energy supplied to said individual's tissue by said source of energy in real time in response to the signal generated by said sensor; and said processor configured to operate said source of energy to provide an adaptive power ramp by which a lower level of energy is initially supplied to the individual's tissue and the output of source of energy supplied to the individual's tissue is gradually increased to a higher level of energy, wherein said power ramp is provided over a predetermined interval during which impedance of the individual's tissue is monitored in real time and change in impedance over time is used to determine a slope of a next power ramp; said processor configured to adjust said power ramp during each interval of energy application based upon a rate of change in impedance over time, wherein a first radiofrequency, RF, pulse for a seal starts at a power level defined as start value, the RF power level is then increased from the start value until the power level reaches an upper level and the RF power level remains at this upper level until the end of the pulse time is reached, at the end of each pulse, the tissue impedance value is calculated and recorded as an RF Pulse End Impedance, and the power levels are then set to zero, for all pulses subsequent to the first, the following evaluations are made, if the RF Pulse End Impedance is less than a threshold, the RF power delivered is ramped similar to the first pulse, and if the RF Pulse End Impedance is greater than said threshold, the RF power delivered is not ramped but stepped directly to said upper level.

9. The apparatus of claim 8, wherein the source of energy is configured to apply energy to said individual's tissue at an initial energy level and increase said energy level to a terminal energy level.

10. The apparatus of claim 9, wherein the source of energy is configured to increase said energy level from said initial energy level to said terminal energy level in any of a series of discrete steps or in a continuous fashion over time.

11. The apparatus of claim 8, further comprising a processor configured to determine when a threshold impedance is reached within a specific interval, said processor configured to apply a constant, predetermined level of energy to said individual's tissue after said threshold impedance is reached and to continue application of said constant, predetermined level of energy to said individual's tissue for a predetermined interval, said processor configured to discontinue application of energy to said individual's tissue after completion of said predetermined interval.

12. The apparatus of claim 8, further comprising a processor configured to determine if said electrosurgical appliance electrodes are partially covered by the individual's tissue or are covered by thin tissue by determining if a rate of change and/or impedance threshold is reached, and thereafter apply a decreasing ramp rate and/or power cutback to prevent over-processing of the tissue.

* * * * *